United States Patent
Obayashi et al.

(10) Patent No.: US 9,572,806 B2
(45) Date of Patent: Feb. 21, 2017

(54) ELUTION-STABILIZED PREPARATION

(75) Inventors: Yasuaki Obayashi, Osaka (JP); Shinichiro Yasui, Aichi (JP); Hidaka Abe, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 88 days.

(21) Appl. No.: 13/516,672

(22) PCT Filed: Dec. 17, 2010

(86) PCT No.: PCT/JP2010/072749
§ 371 (c)(1),
(2), (4) Date: Jul. 23, 2012

(87) PCT Pub. No.: WO2011/074660
PCT Pub. Date: Jun. 23, 2011

(65) Prior Publication Data
US 2012/0276166 A1    Nov. 1, 2012

(30) Foreign Application Priority Data
Dec. 18, 2009 (JP) ................................. 2009-287809

(51) Int. Cl.
A61K 31/496 (2006.01)
A61K 9/00 (2006.01)
A61P 3/10 (2006.01)
A61K 9/20 (2006.01)
A61K 9/28 (2006.01)

(52) U.S. Cl.
CPC ........... *A61K 31/496* (2013.01); *A61K 9/0019* (2013.01); *A61K 9/2018* (2013.01); *A61K 9/2866* (2013.01)

(58) Field of Classification Search
None
See application file for complete search history.

(56) References Cited

U.S. PATENT DOCUMENTS

| 7,074,794 | B2 * | 7/2006 | Kitajima et al. | 514/252.12 |
| 8,003,790 | B2 | 8/2011 | Yoshida et al. | |
| 2004/0106655 | A1 * | 6/2004 | Kitajima | C07D 207/16 514/365 |
| 2005/0169986 | A1 * | 8/2005 | Tian | A61K 9/0056 424/464 |
| 2006/0153916 | A1 * | 7/2006 | Vaya et al. | 424/470 |
| 2008/0038341 | A1 * | 2/2008 | Kowalski | A61K 9/2013 424/465 |
| 2009/0088442 | A1 * | 4/2009 | Abe | C07D 417/14 514/254.02 |
| 2009/0318482 | A1 | 12/2009 | Ono et al. | |

FOREIGN PATENT DOCUMENTS

| EP | 185108 A1 * | 6/1986 | |
| EP | 1 852 108 A1 | 11/2007 | |
| EP | 1 854 795 A1 | 11/2007 | |
| EP | 1854795 A1 * | 11/2007 | |
| EP | 1 882 474 A1 | 1/2008 | |
| WO | WO 02/14271 A1 | 2/2002 | |
| WO | WO 2006/088129 A1 | 8/2006 | |
| WO | WO 2006/118127 A1 | 11/2006 | |
| WO | WO 2006118127 A1 * | 11/2006 | A61K 31/496 |
| WO | WO 2008/093878 A1 | 8/2008 | |
| WO | WO 2009111200 A1 * | 9/2009 | |

OTHER PUBLICATIONS

P. Rajniak, C. Mancinelli, R.T. Chern, F. Stepanek, L. Farber, B.T. Hill. Experimental study of wet granulation in fluidized bed: Impact of the binder properties on the granule morphology. International Journal of Pharmaceutics 334 (2007) 92-102.*
Product specification of Pearlitol 200 SD from Signet Chemical, downloaded Feb. 23, 2014, from the internet site: http://www.signetchem.com/Signet-The-Complete-Company-Product-Pearlitol.*
Jiho, Inc., "General aspects—Basic knowledge of formulation technique toward effective utilization of additive," *Iyakuhin Tenkazai Youran*, p. 17 (Nov. 25, 1992).
Ozeki et al., *Yakuzaigaku*, 64(1): 59-66 (2004).
European Patent Office, Extended European Search Report in European Patent Application No. 10837684.9 (Apr. 25, 2013).
Japanese Patent Office, International Search Report in International Patent Application No. PCT/JP2010/072749 (Mar. 15, 2011).

* cited by examiner

*Primary Examiner* — Frederick Krass
*Assistant Examiner* — Michael P Cohen
(74) *Attorney, Agent, or Firm* — Leydig, Voit & Mayer, Ltd.

(57) ABSTRACT

The invention provides a solid preparation which does not undergo the delay of elution of the active ingredient even after long-term storage. The solid preparation independently contains a teneligliptin-containing part containing teneligliptin or a salt thereof, or a solvate of teneligliptin or the salt thereof, in an amount 1.5- to 10-fold larger than that desired for the solid preparation.

7 Claims, 12 Drawing Sheets

ELUTION-STABILIZED PREPARATION

CROSS-REFERENCE TO RELATED APPLICATIONS

This patent application is the U.S. national phase of International Patent Application No. PCT/JP2010/072749, filed Dec. 17, 2010, which claims the benefit of Japanese Patent Application No. 2009-287809, filed Dec. 18, 2009, which are incorporated by reference in their entireties.

TECHNICAL FIELD

The present invention relates to a teneligliptin-containing solid preparation that causes less delay in a dissolution behavior of the active ingredient, even after a long-term preservation.

BACKGROUND ART

Teneligliptin [chemical name: {(2S,4S)-4-[4-(3-methyl-1-phenyl-1H-pyrazol-5-yl)piperazin-1-yl]-pyrrolidin-2-yl}(1,3-thiazolidin-3-yl)methanone] is a compound represented by the formula (I):

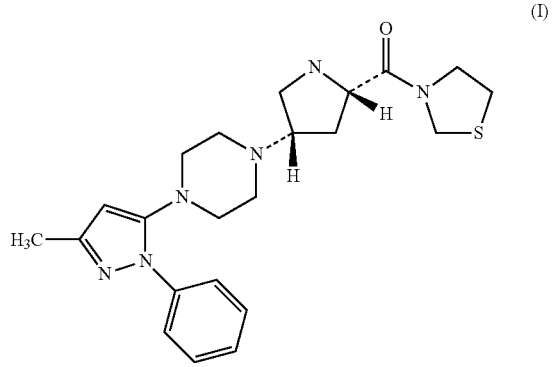

and 5/2 hydrobromide.hydrate thereof is under clinical development as a therapeutic drug for type 2 diabetes, based on a potent and sustained dipeptidyl peptidase-IV inhibitory action.

As a formulation or production method of a solid preparation containing teneligliptin or a salt thereof, or a solvate thereof (hereinafter sometimes to be abbreviated as a teneligliptin-containing solid preparation), it is known that teneligliptin or a salt thereof, or a solvate thereof and a conventional carrier for medicaments are mixed and formulated (see patent documents 1 and 2).

The present inventors have produced a teneligliptin-containing solid preparation having a conventional pharmaceutical formulation for production of a solid preparation, and investigated the quality of the preparation. As a result, they have confirmed that a long-term preservation of a teneligliptin-containing solid preparation having a particular content for about several months causes delayed dissolution of teneligliptin or a salt thereof, or a solvate thereof, which is the active ingredient.

While an influence of such delay in the dissolution over time of the active ingredient on the efficacy of a pharmaceutical product is not easy to predict accurately, a preparation showing a stable dissolution behavior is considered to be more preferable as a pharmaceutical product.

DOCUMENT LIST

Patent Documents patent document 1: WO02/014271
patent document 2: WO2006/088129

SUMMARY OF THE INVENTION

Problems to be Solved by the Invention

The present invention aims to solve the above-mentioned problems relating to a solid preparation with a conventional formulation, which contains teneligliptin or a salt thereof, or a solvate thereof as an active ingredient, and provides a teneligliptin-containing solid preparation that causes less delay in a dissolution behavior of the active ingredient, even after a long-term preservation.

Means of Solving the Problems

The present inventors have conducted intensive studies in an attempt to solve the aforementioned problems and found that a teneligliptin-containing solid preparation with suppressed delay in dissolution with time, which is caused by a long-term preservation, can be obtained by preparing a teneligliptin-containing part containing teneligliptin or a salt thereof, or a solvate thereof at a content percentage corresponding to several times that desired for a final solid preparation, and independently including the same in the solid preparation, and further studied differences in the effect and the like due to the kind of excipient that the solid preparation can contain in a part other than the teneligliptin-containing part, which resulted in the completion of the present invention.

The summary of the present invention includes the following [1] to [13].

[1] A teneligliptin-containing solid preparation independently comprising a teneligliptin-containing part containing teneligliptin or a salt thereof, or a solvate thereof at a content percentage 1.5- to 10-fold the content percentage desired for a solid preparation.

[2] The solid preparation of the above-mentioned [1], comprising an excipient in a part other than the teneligliptin-containing part.

[3] The solid preparation of the above-mentioned [2], wherein the excipient contained in a part other than the teneligliptin-containing part is one or more kinds selected from D-mannitol, sorbitol and xylitol.

[4] The solid preparation of the above-mentioned [2] or [3], wherein the excipient contained in the part other than the teneligliptin-containing part has a volume average particle diameter of 50 μm to 500 μm.

[5] The solid preparation of the above-mentioned [4], wherein the excipient contained in the part other than the teneligliptin-containing part has a volume average particle diameter of 100 μm to 300 μm.

[6] The solid preparation of any of the above-mentioned [1] to [5], wherein the teneligliptin or a salt thereof, or a solvate thereof is teneligliptin hydrobromide.hydrate.

[7] The solid preparation of any of the above-mentioned [1] to [6], wherein the teneligliptin-containing part contains D-mannitol or xylitol.

[8] The solid preparation of any of the above-mentioned [1] to [7], wherein the teneligliptin-containing part is particulate, granular or aggregatus.

[9] The solid preparation of any of the above-mentioned [1] to [8], wherein the content percentage of tenegliptin or a salt thereof, or a solvate thereof in the tenegliptin-containing part is 30 to 80 wt %, the part other than the tenegliptin-containing part contains one or more kinds of excipients selected from D-mannitol, sorbitol and xylitol.

[10] The solid preparation of the above-mentioned [9], wherein the tenegliptin or a salt thereof, or a solvate thereof is tenegliptin hydrobromide.hydrate.

[11] The solid preparation of the above-mentioned [9] or [10], wherein the content percentage is 45 to 55 wt %.

[12] A production method of a tenegliptin-containing solid preparation, comprising
(1) a step of obtaining a tenegliptin-containing composition containing tenegliptin hydrobromide.hydrate at a content percentage 1.5- to 10-fold that desired for the solid preparation,
(2) a step of mixing the obtained tenegliptin-containing composition with one or more kinds of excipients selected from D-mannitol, sorbitol and xylitol, and a pharmaceutically acceptable additive, and
(3) a step of tableting the obtained mixture.

[13] The production method of the above-mentioned [12], wherein tenegliptin hydrobromide.hydrate in the tenegliptin-containing composition has a content percentage of 45 to 55 wt %.

Effect of the Invention

According to the present invention, a tenegliptin-containing solid preparation showing suppressed delay in dissolution with time of tenegliptin or a salt thereof, or a solvate thereof, which is the active ingredient, even after a long-term preservation (hereinafter sometimes to be referred to as the solid preparation of the present invention) can be provided. As a result, when a tenegliptin-containing solid preparation is administered to a target, the blood concentration of the active ingredient in the body can be stabilized under certain conditions.

DESCRIPTION OF EMBODIMENTS

Figure 1:
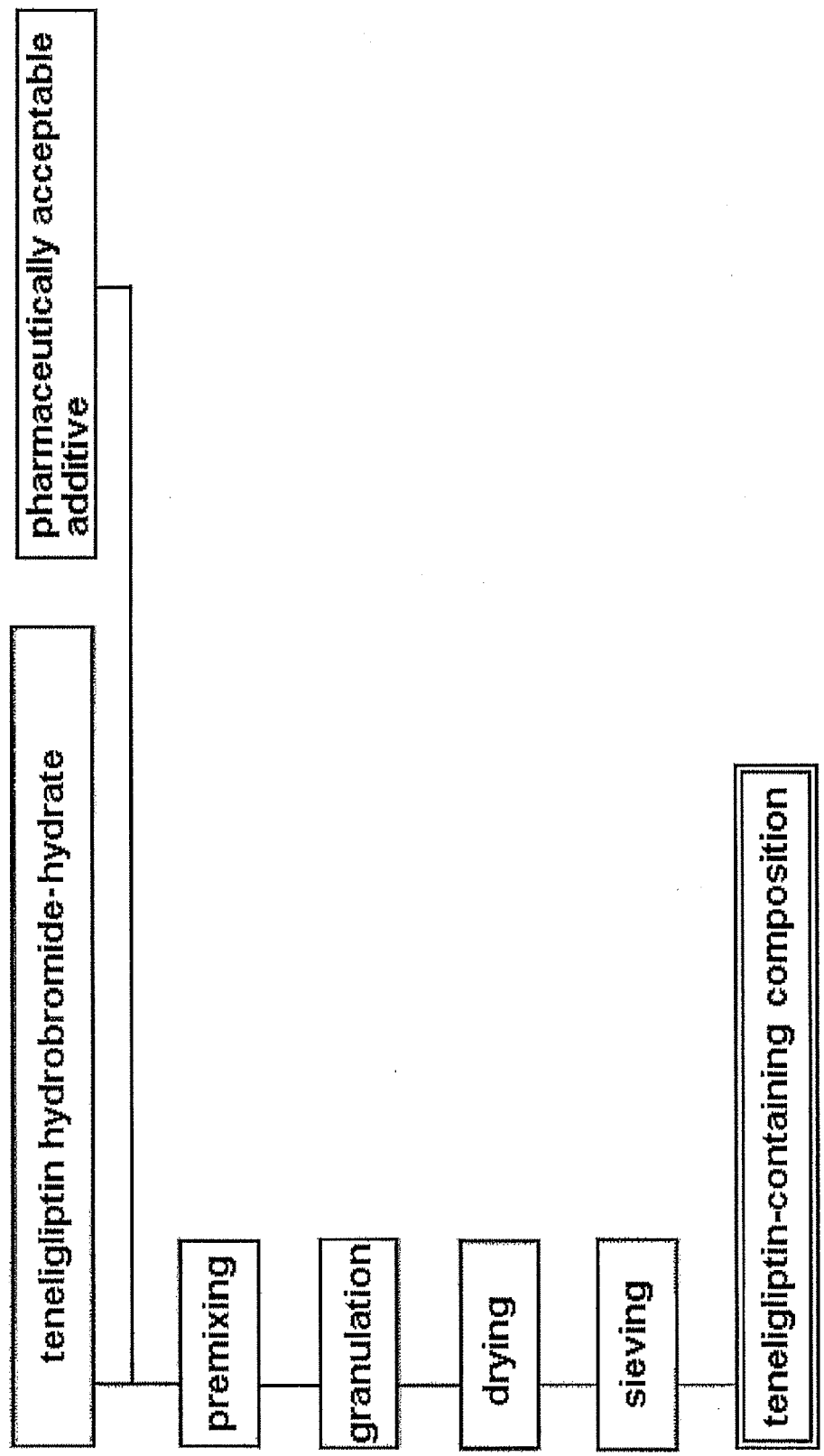
FIG. 1 shows one embodiment of step (1) in the production method of a tenegliptin-containing solid preparation.

Tenegliptin or a salt thereof, or a solvate thereof to be used for the production of the solid preparation of the present invention is a known compound described in WO02/014271 and WO2006/088129, and can be synthesized by the methods described in these documents. Tenegliptin or a salt thereof, or a solvate thereof to be used for the solid preparation of the present invention is preferably tenegliptin hydrobromide.hydrate, more preferably tenegliptin 5/2 hydrobromide.hydrate, more preferably 1.0-2.0 hydrate of tenegliptin 5/2 hydrobromide.

In the present invention, the "tenegliptin-containing part" is a part containing tenegliptin or a salt thereof, or a solvate thereof at a content percentage corresponding to several times that desired for a final solid preparation. This part preferably contains tenegliptin or a salt thereof, or a solvate thereof at a content percentage 1.5- to 10-fold that desired for the solid preparation of the present invention.

The above-mentioned "tenegliptin-containing part" containing tenegliptin or a salt thereof, or a solvate thereof at a high concentration not less than a certain level is advantageous in that it is free of delayed dissolution of the active ingredient even after a long-term preservation.

When the content percentage of tenegliptin or a salt thereof, or a solvate thereof in said part is less than 1.5-fold that desired for the solid preparation of the present invention, the object of prevention of delay in the dissolution of the active ingredient cannot be achieved, whereas when it is higher than 10-fold, the lack of strength necessary for maintaining the solid form of particles and the like is feared, and the possibility of problem in the production cannot be denied.

The part is produced according to a method known in the technical field of the pharmaceutical preparations, by appropriately mixing tenegliptin or a salt thereof, or a solvate thereof with an appropriate amount of at least one kind of pharmaceutically acceptable additive and the like.

The content percentage of tenegliptin or a salt thereof, or a solvate thereof in the tenegliptin-containing part is not limited as long as the above-mentioned fold magnification relative to the content percentage of tenegliptin or a salt thereof, or a solvate thereof, which is desired in the solid preparation of the present invention, can be achieved, and it is generally 30 to 80 wt %, preferably 45 to 55 wt %, of the part as a whole.

When the content percentage of tenegliptin or a salt thereof, or a solvate thereof in the part is less than 30 wt % of the part as a whole, the object of prevention of delay in the dissolution of the active ingredient cannot be achieved, whereas when it is higher than 80 wt %, the lack of strength necessary for maintaining the solid form of particles and the like is feared, and the possibility of problem in the production cannot be denied.

As the "pharmaceutically acceptable additive" that can be added to the teneligliptin-containing part, various organic or inorganic carrier substances conventionally used as preparation materials can be mentioned. Examples of thereof include excipient, lubricant, binder, fluidizer, disintegrant, solubilizing agent and the like. Preferred are excipient, binder, fluidizer and disintegrant, and more preferred is excipient.

Preferable examples of the excipient include D-mannitol, sorbitol, xylitol, cornstarch, potato starch, lactose, crystalline cellulose, calcium hydrogen phosphate and the like can be mentioned, preferably, D-mannitol, xylitol, and cornstarch.

Preferable examples of the lubricant include magnesium stearate, calcium stearate, talc, stearic acid, sucrose ester of fatty acid and the like.

Preferable examples of the binder include hydroxypropylcellulose, polyvinyl alcohol, povidone, hypromellose, carmellose sodium, methylcellulose and the like.

Preferable examples of the fluidizer include light anhydrous silicic acid, hydrated silicon dioxide, talc and the like.

Preferable examples of the disintegrant include low-substituted hydroxypropylcellulose, sodium carboxymethyl starch, carmellose calcium, crospovidone and the like.

Preferable examples of the solubilizing agents include sodium benzoate, ethylenediamine, potassium iodide and the like.

The teneligliptin-containing part in the solid preparation of the present invention is generally solid. Its shape is not particularly limited as long as, as mentioned below, it enables the part to be independently present in the solid preparation of the present invention, and may be either particulate, granular or aggregatus, preferably particulate.

The particle diameter of the part is not particularly limited. It preferably has a volume average particle diameter (hereinafter to be indicated as "D50") of not more than 350 μm and a particle diameter of not less than 90% of the particles of not more than 500 μm, more preferably, D50 of not more than 180 μm and a particle size of not less than 90% of the particles of not more than 250 μm.

The term "volume average particle diameter" used in the present specification refers to an average particle diameter based on the volume corresponding to the values of the particles. In principle, it means a particle diameter of a particle corresponding to 50% volume when particles having predetermined volume are sequentially sieved from smaller ones. The volume average particle diameter can be measured according to a conventional method in the technical field, which includes, for example, measurement by microscopic observation, a method using an electric or optical particle diameter measuring apparatus and the like. Particularly, the volume average particle diameter of a powder having a particle size of several dozen—a few hundred μm is mainly measured by a sieving method, a method including dispersing the powder in a medium and measuring the particle diameter by utilizing diffracted light or scattering light and the like. The sieving method include use of plural sieves with different apertures, wherein the sieves are layered such that one having a larger aperture is placed on the upper panel, a powder to be measured is supplied into the top panel, the sieve is vibrated manually or mechanically, the amount of the powder left on each sieve is measured and the weight fraction is calculated.

The part can be produced as particles etc. by subjecting, according to a method known in the technical field of the pharmaceutical preparations, a mixture of teneligliptin or a salt thereof, or a solvate thereof and at least one kind of pharmaceutically acceptable additive and the like to wet granulation by, for example, a fluidized bed granulation method and drying. The thus-obtained teneligliptin-containing part has a strength permitting independent existence in the solid preparation of the present invention. When the teneligliptin-containing part is particulate or granular, the part can be present by being dispersed in the solid preparation of the present invention.

The teneligliptin-containing part being aggregatus means, in the absence of technical limitation on tableting, that the particle diameter of the teneligliptin-containing part is set large and the solid preparation of the present invention contains one to several teneligliptin-containing parts. A nucleated tablet containing one teneligliptin-containing part as a core in the solid preparation of the present invention is also encompassed in the scope of the present invention.

The solid preparation of the present invention "independently comprising" the above-mentioned teneligliptin-containing part means that the teneligliptin-containing part and other parts (hereinafter sometimes to be referred to as a teneligliptin-non-containing part) in the solid preparation are not miscible with each other and have different disintegration rates. The teneligliptin-non-containing part preferably has a faster disintegration rate than the teneligliptin-containing part and is disintegrated without delay in the subject.

The "teneligliptin-non-containing part" in the solid preparation of the present invention is not particularly limited as long as it does not contain teneligliptin or a salt thereof, or a solvate thereof, and can adjust the content percentage of teneligliptin or a salt thereof, or a solvate thereof in the solid preparation of the present invention to a desired level. As mentioned above, the "teneligliptin-non-containing part" is desired to have a faster disintegration rate than the teneligliptin-containing part.

The teneligliptin-non-containing part can contain one or more kinds of pharmaceutically acceptable additives within the range not impairing the effect of the present invention. As the "pharmaceutically acceptable additive", those similar to the "pharmaceutically acceptable additives" that can be contained in the above-mentioned teneligliptin-containing part can be mentioned.

Particularly, the teneligliptin-non-containing part preferably contains one or more kinds of excipient. As such excipient, sugar alcohol is preferable, and specific examples thereof include xylitol, D-mannitol, sorbitol and the like, with more preference given to D-mannitol. While the particle diameter of the excipient is not particularly limited, D50 is preferably 50 μm-500 μm, more preferably 100 μm-300 μm, to increase the disintegration rate. Such excipient can also be obtained as a commercially available product.

The content percentage of the excipient in the "teneligliptin-non-containing part" of the solid preparation of the present invention can be adjusted according to the desired content percentage of teneligliptin or a salt thereof, or a solvate thereof in the solid preparation of the present invention, and is preferably 30-80 wt %, more preferably 35-55 wt %.

The solid preparation of the present invention may be coated with a coating solution containing hypromellose, macrogol 400, titanium oxide, red ferric oxide and the like.

While the content percentage of teneligliptin or a salt thereof, or a solvate thereof in the solid preparation of the present invention is not particularly limited, it is preferably 5-60 wt %, more preferably 10-30 wt %.

As the solid preparation of the present invention, one independently containing a teneligliptin-containing part containing teneligliptin hydrobromide.hydrate at a content percentage of 30-80 wt % (in the teneligliptin-containing part), and additionally containing one or more kinds of excipients selected from D-mannitol, sorbitol and xylitol is preferable, and one having a content percentage of teneligliptin hydrobromide.hydrate of 45-55 wt % (in the teneligliptin-containing part) is more preferable.

The solid preparation of the present invention designed as mentioned above has a high concentration of teneligliptin or a salt thereof, or a solvate thereof in the "teneligliptin-containing part", and therefore, is advantageous in that it is free of delayed dissolution of the active ingredient even after a long-term preservation. In addition, since the solid preparation has a sufficient size as a preparation, it satisfies "easy removal from the package", "resistance to rolling", "easy holding" and the like required from the aspects of administration compliance. The solid preparation of the present invention shows rapid disintegration of the "teneligliptin-non-containing part" to release the "teneligliptin-containing part" and exhibits efficacy.

The solid preparation of the present invention is produced by, for example, a production method containing the following steps:
(1) a step of obtaining a teneligliptin-containing composition containing teneligliptin hydrobromide.hydrate at a content percentage 1.5- to 10-fold that desired for the solid preparation,
(2) a step of mixing the obtained teneligliptin-containing composition with one or more kinds of excipients selected from D-mannitol, sorbitol and xylitol, and a pharmaceutically acceptable additive, and
(3) a step of tableting the obtained mixture.

In the above-mentioned step (1), the content percentage of teneligliptin or a salt thereof, or a solvate thereof is adjusted to 1.5- to 10-fold that desired for the solid preparation by mixing with a pharmaceutically acceptable additive.

For example, when the teneligliptin-containing composition is particulate or granular, the obtained mixture is granulated, dried, sieved and the like to give a teneligliptin-containing composition. One embodiment of the step is shown in FIG. 1.

The content percentage of teneligliptin hydrobromide.hydrate in the teneligliptin-containing composition is preferably 30-80 wt %, more preferably 45-55 wt %.

In the above-mentioned step (2), the obtained teneligliptin-containing composition is mixed with one or more kinds of excipients selected from D-mannitol, sorbitol and xylitol, and other pharmaceutically acceptable additive. In the mixture, the teneligliptin-containing composition is present independently of other parts.

Figure 2:
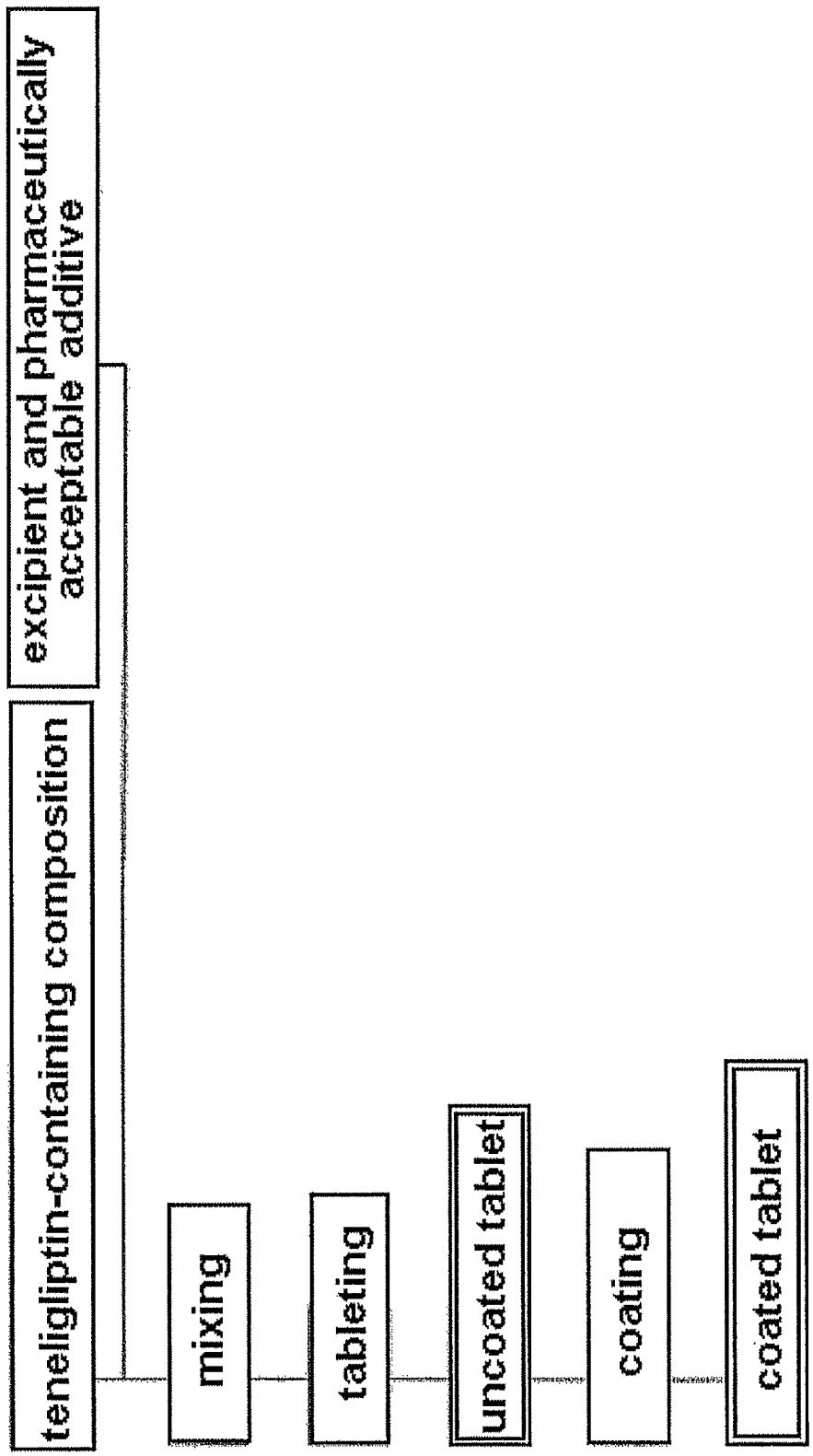
FIG. 2 shows one embodiment of each step including steps (2) and (3) in the production method of a tenegliptin-containing solid preparation.

In the above-mentioned step (3), the obtained mixture is molded by tableting. Where necessary, the obtained core tablet may be coated to give a coated tablet. One embodiment of respective steps including steps (2) and (3) is shown in FIG. 2.

The solid preparation of the present invention can be administered orally to a human, as well as mammals other than human (e.g., mouse, rat, hamster, guinea pig, rabbit, cat, dog, swine, bovine, horse, sheep, monkey etc.).

The dose of the solid preparation of the present invention is determined according to the age, body weight, general health condition, sex, diet, administration time, administration method, clearance rate, combination of drugs, and the level of the disease state of patients under treatment, and in consideration of other factors. The solid preparation of the present invention is low toxic and can be used safely. The daily dose varies depending on the condition, body weight and the like of patients and, for example, 0.01-100 mg/kg body weight/day, preferably 0.05-50 mg/kg body weight/day, of teneligliptin as the active ingredient is preferably administered in one to several portions per day.

EXAMPLES

The present invention is explained in detail in the following by referring to Examples, which are not to be construed as limitative.

Unless otherwise specified, the additives used for the production of the preparations in Comparative Examples and Examples such as excipient and the like were as follows.
D-mannitol (Roquette, model number: Pearlitol 200SD)
cornstarch (Roquette, model number: extra white maize starch) light anhydrous silicic acid (Merk, model number: silicon dioxide)
hydroxypropylcellulose (Nippon Soda Co., Ltd., model number: HPC-L)
low-substituted hydroxypropylcellulose (Shin-Etsu Chemical Co., Ltd., model number: L-HPC LH-11)
magnesium stearate (Merk, model number: plant-derived)
hypromellose (Shin-Etsu Chemical Co., Ltd., model number: TC-5R)
macrogol 400 (NOF Corporation, model number: macrogol 400R)
titanium oxide (ISHIHARA SANGYO KAISHA, LTD., model number: A-100)
red ferric oxide (Kishi Kasei Co., Ltd., model number: red ferric oxide)
fluid bed granulator (Freund Corporation, model number: FLO-5M)
rotary tableting machine (Kikusui Seisakusho Ltd., model number: VIRGO518SS2AZ)
Teneligliptin 5/2 hydrobromide.1.8 hydrate was synthesized according to the method described in WO02/014271 and WO2006/088129.

Comparative Example 1

Production of Teneligliptin 5 mg Tablet (1) Teneligliptin 5/2 hydrobromide.1.8 hydrate (6.20 wt %), D-mannitol (60.00 wt %), cornstarch (15.88 wt %) and light anhydrous silicic acid (0.48 wt %) were mixed. Using a fluid bed granulator, the mixture was granulated using an aqueous solution containing hydroxypropylcellulose (2.88 wt %), dried and sieved to give a granulated powder.
(2) to the granulated powder obtained in the above-mentioned (1) were added low-substituted hydroxypropylcellulose (9.60 wt %) and magnesium stearate (0.96 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet.

Comparative Example 2

Production of Teneligliptin 10 mg Tablet (1) Teneligliptin 5/2 hydrobromide.1.8 hydrate (12.32 wt %), D-mannitol (48.00 wt %), cornstarch (12.16 wt %), low-substituted hydroxypropylcellulose (9.60 wt %) and light anhydrous silicic acid (0.48 wt %) were mixed. Using a fluid bed granulator, the mixture was granulated using an aqueous solution containing hydroxypropylcellulose (2.88 wt %), dried and sieved to give a granulated powder.

(2) to the granulated powder obtained in the above-mentioned (1) were added low-substituted hydroxypropylcellulose (9.60 wt %) and magnesium stearate (0.96 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet.

Comparative Example 3

Production of Teneligliptin 20 mg Tablet (1) Teneligliptin 5/2 hydrobromide.1.8 hydrate (24.80 wt %), D-mannitol (48.00 wt %), cornstarch (9.28 wt %) and light anhydrous silicic acid (0.48 wt %) were mixed. Using a fluid bed granulator, the mixture was granulated using an aqueous solution containing hydroxypropylcellulose (2.88 wt %), dried and sieved to give a granulated powder.

(2) to the granulated powder obtained in the above-mentioned (1) were added low-substituted hydroxypropylcellulose (9.60 wt %) and magnesium stearate (0.96 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet.

Example 1

Production of Teneligliptin-Containing Part (1) Teneligliptin 5/2 hydrobromide.1.8 hydrate (52.45 wt %), D-mannitol (33.84 wt %), cornstarch (10.15 wt %) and light anhydrous silicic acid (0.51 wt %) were mixed. Using a fluid bed granulator, the mixture was granulated using an aqueous solution containing hydroxypropylcellulose (3.05 wt %), dried and sieved to give a granulated powder (hereinafter sometimes to be abbreviated as teneligliptin granulated powder).

Example 2

Production of Teneligliptin-Containing Solid Preparation (Teneligliptin 5 mg Tablet)

To the teneligliptin granulated powder (11.82 wt %) obtained in the above-mentioned Example 1 were added D-mannitol (74.10 wt %), low-substituted hydroxypropylcellulose (9.60 wt %) and magnesium stearate (0.48 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet (8-fold diluted tablet of teneligliptin granulated powder).

Example 3

Production of Teneligliptin Solid Preparation (Teneligliptin 10 mg Tablet)

To the teneligliptin granulated powder (23.64 wt %) obtained in the above-mentioned Example 1 were added D-mannitol (62.28 wt %), low-substituted hydroxypropylcellulose (9.60 wt %) and magnesium stearate (0.48 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet (4-fold diluted tablet of teneligliptin granulated powder).

Example 4

Production of Teneligliptin Solid Preparation (Teneligliptin 20 mg Tablet)

To the teneligliptin granulated powder (47.28 wt %) obtained in the above-mentioned Example 1 were added D-mannitol (38.64 wt %), low-substituted hydroxypropylcellulose (9.60 wt %) and magnesium stearate (0.48 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet (2-fold diluted tablet of teneligliptin granulated powder).

Example 5

Production of Teneligliptin Solid Preparation Using Xylitol (Teneligliptin 10 mg Tablet)

To the teneligliptin granulated powder (23.64 wt %) obtained in the above-mentioned Example 1 were added xylitol (manufactured by Mitsubishi Chemical Corporation, Xylit finely-divided powder) (61.80 wt %), low-substituted hydroxypropylcellulose (9.60 wt %), light anhydrous silicic acid (0.48 wt %) and magnesium stearate (0.48 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet (4-fold diluted tablet of teneligliptin granulated powder).

Example 6

Production of Teneligliptin Solid Preparation Using Sorbitol (Teneligliptin 10 mg Tablet)

To the teneligliptin granulated powder (23.64 wt %) obtained in the above-mentioned Example 1 were added sorbitol (manufactured by Nikken Kasei, sorbit DP-50M) (62.28 wt %), low-substituted hydroxypropylcellulose (9.60 wt %) and magnesium stearate (0.48 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %)

was sprayed on the uncoated tablet to give a 125 mg coated tablet (4-fold diluted tablet of tenegliptin granulated powder).

Example 7

Production of Tenegliptin Solid Preparation Using Finely-Divided Mannitol Powder (Tenegliptin 10 mg Tablet)

To the tenegliptin granulated powder (23.64 wt %) obtained in the above-mentioned Example 1 were added D-mannitol (manufactured by Merk, fine powder: D-mannitol powder containing not less than 15% of particles having a particle diameter of 20 μm or below) (62.28 wt %), low-substituted hydroxypropylcellulose (9.60 wt %) and magnesium stearate (0.48 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet (4-fold diluted tablet of tenegliptin granulated powder).

Example 8

Production of Tenegliptin Solid Preparation Using Mannitol (Tenegliptin 10 mg Tablet)

To the tenegliptin granulated powder (23.64 wt %) obtained in the above-mentioned Example 1 were added D-mannitol (manufactured by Roquette, Pearlitol 500DC: D-mannitol powder having a volume average particle diameter of 500 μm) (62.28 wt %), low-substituted hydroxypropylcellulose (9.60 wt %) and magnesium stearate (0.48 wt %), and the mixture was compression molded in a rotary tableting machine to give an uncoated tablet. A coating solution containing hypromellose (2.50 wt %), macrogol 400 (0.25 wt %), titanium oxide (1.23 wt %) and red ferric oxide (0.02 wt %) was sprayed on the uncoated tablet to give a 125 mg coated tablet (4-fold diluted tablet of tenegliptin granulated powder).

Experimental Example 1

Comparative Test of Dissolution Ratio of Preparation Before and After Preservation The preparations obtained in Comparative Examples 1-3 and Examples 2-4 were blister packaged and subjected to an acceleration test. The dissolution ratio of tenegliptin 5/2 hydrobromide (hereinafter indicated as the main drug) was compared between before preservation and after preservation (40° C., 75% RH, 3 months or 6 months). The dissolution ratio was calculated by adding the preparations before and after preservation to the Japanese Pharmacopoeia Second Solution (900 mL) heated to 37° C., stirring the mixture at paddle rotation 50 rpm and measuring the concentration of the main drug over time.

Figure 3:
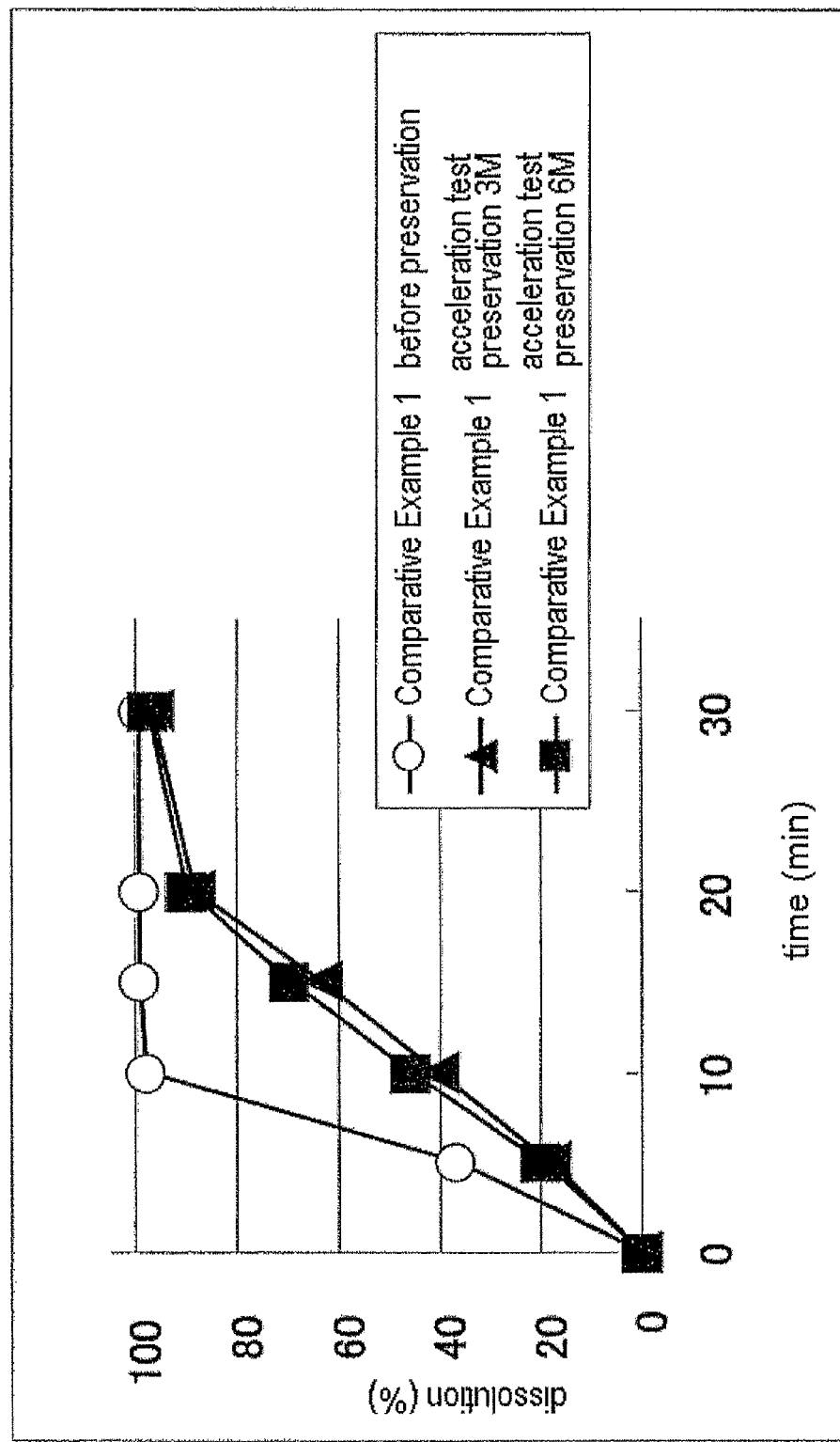
FIG. 3 shows the comparison results of the dissolution ratios of the preparation of Comparative Example 1 before and after preservation.
Figure 4:
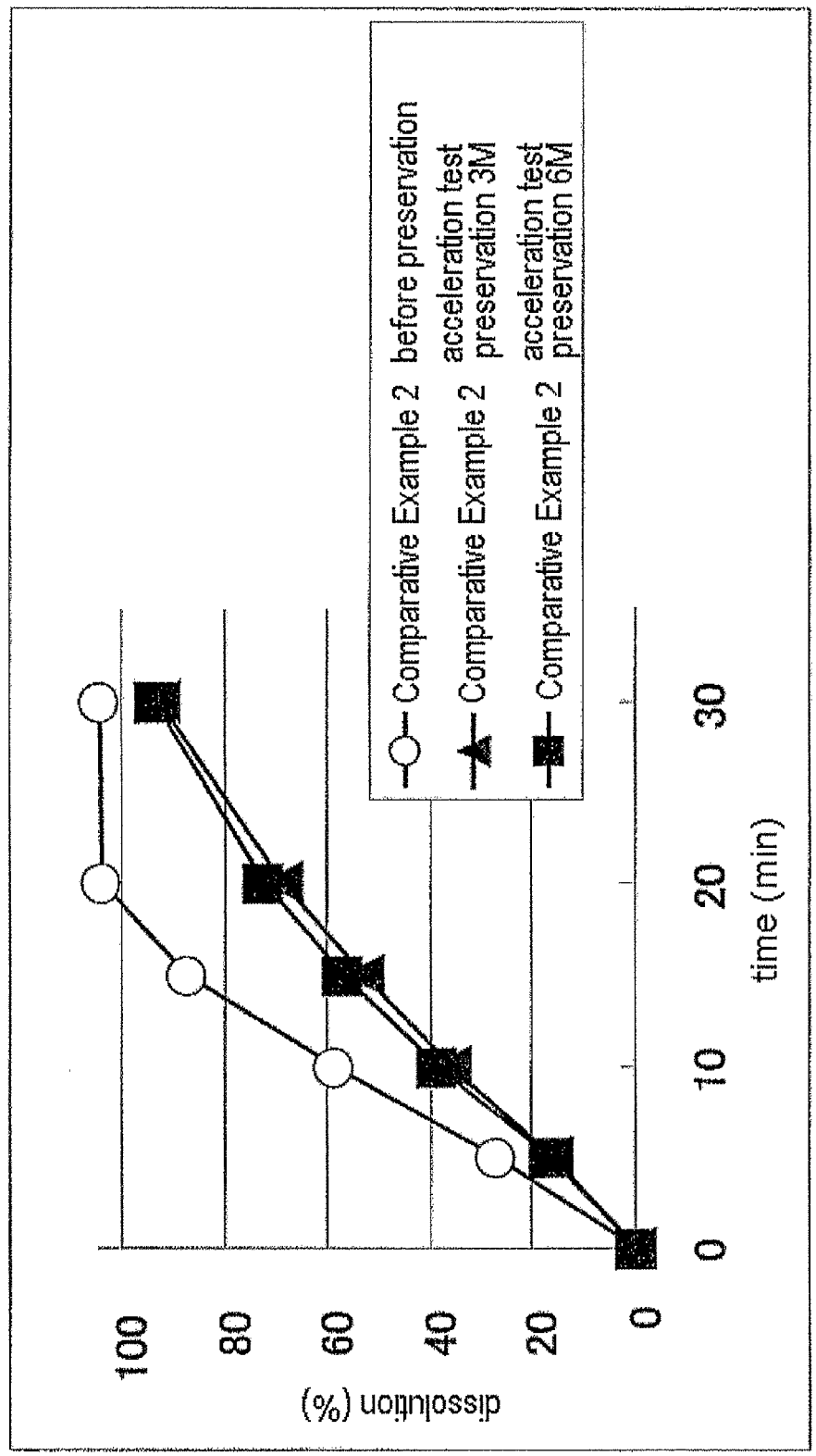
FIG. 4 shows the comparison results of the dissolution ratios of the preparation of Comparative Example 2 before and after preservation.
Figure 5:
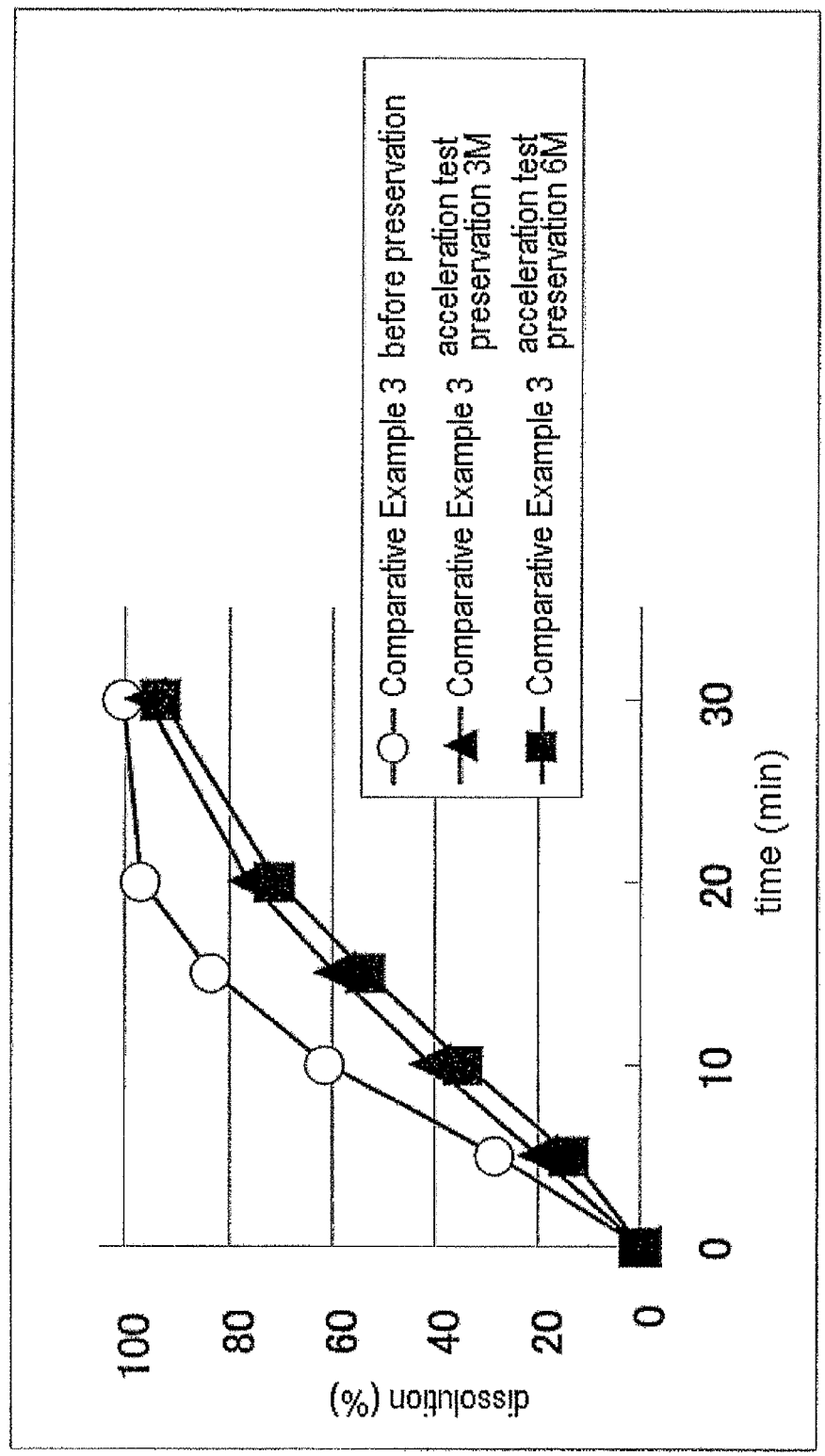
FIG. 5 shows the comparison results of the dissolution ratios of the preparation of Comparative Example 3 before and after preservation.
Figure 6:
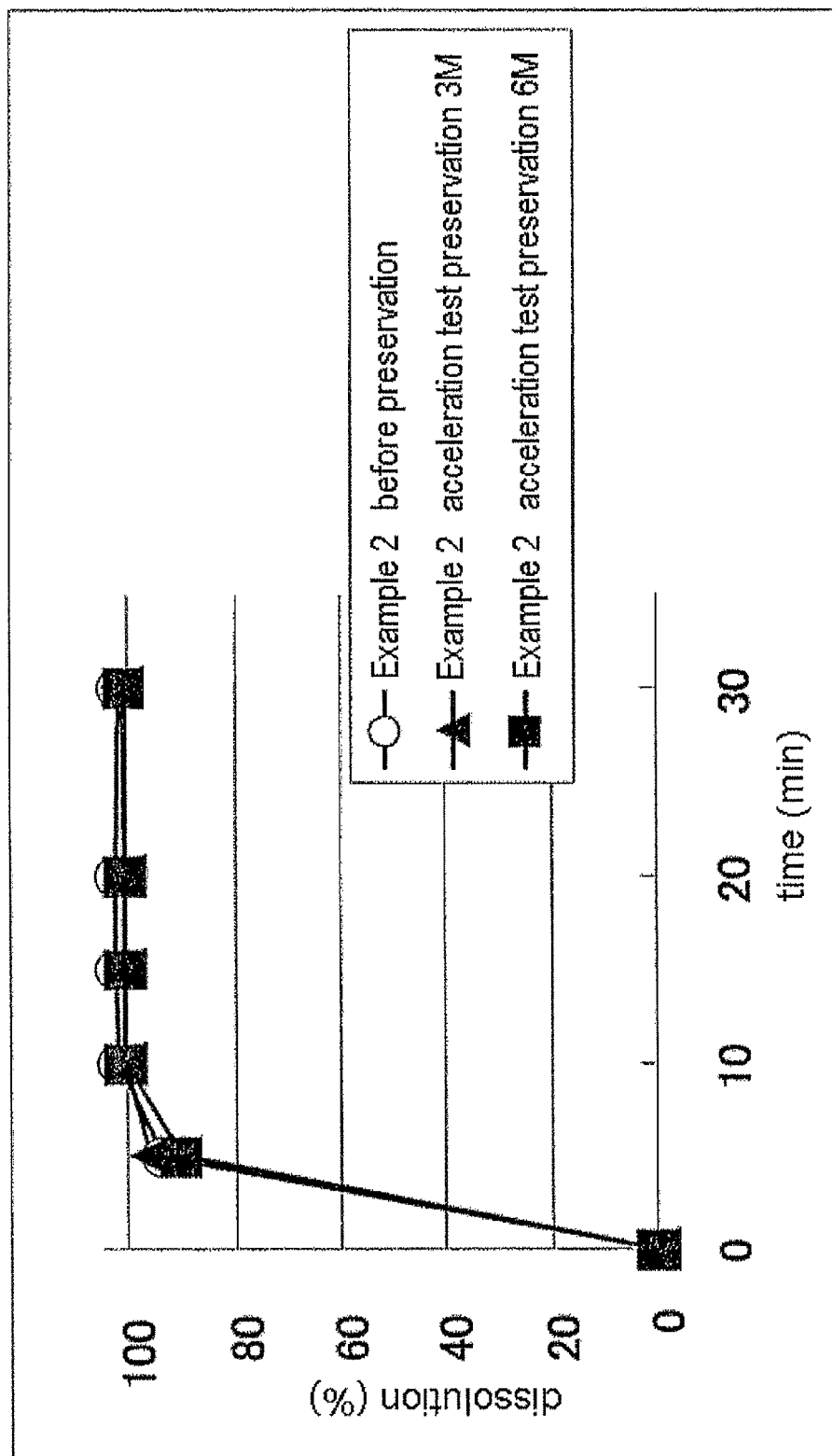
FIG. 6 shows the comparison results of the dissolution ratios of the preparation of Example 2 before and after preservation.
Figure 7:
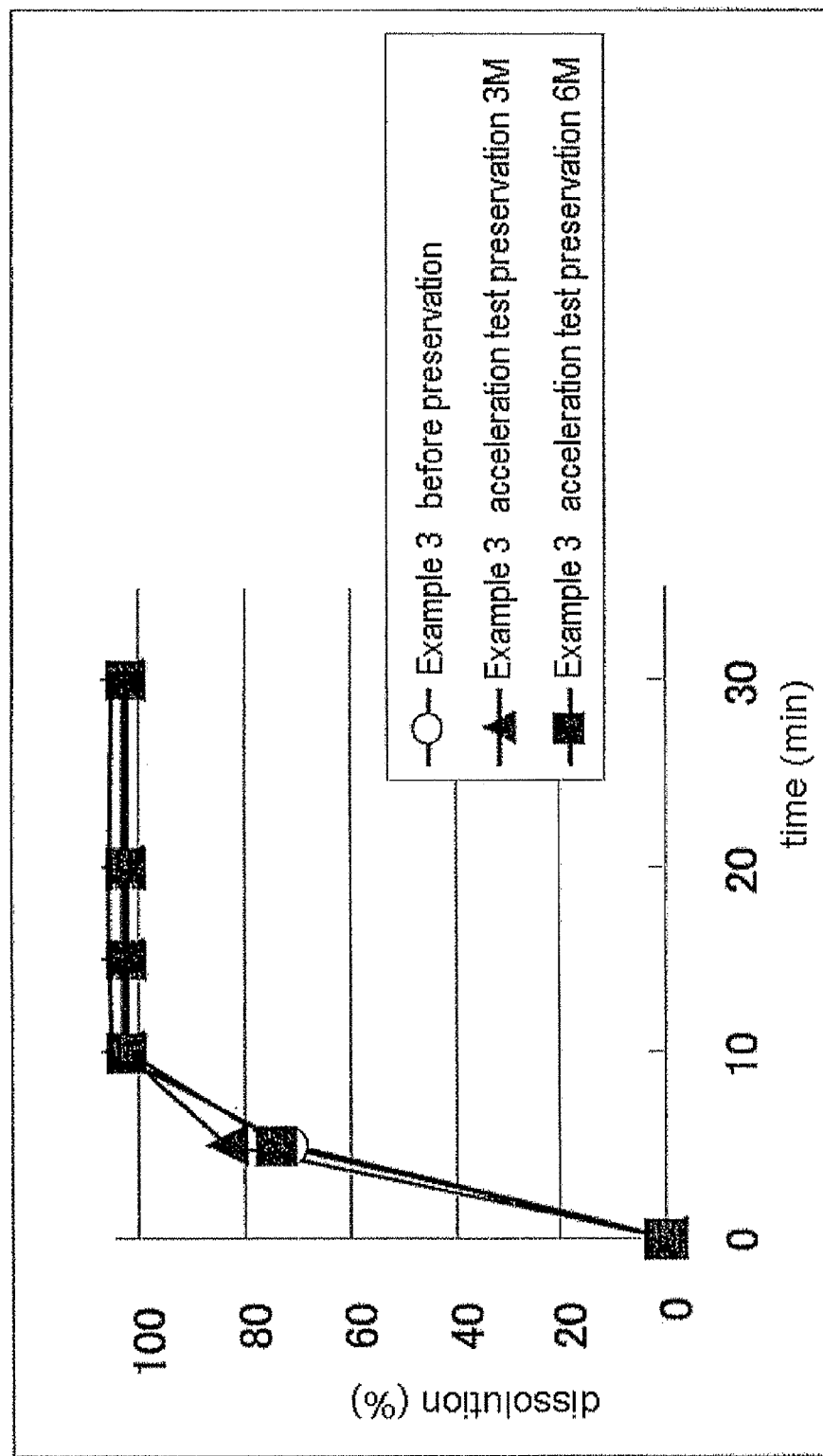
FIG. 7 shows the comparison results of the dissolution ratios of the preparation of Example 3 before and after preservation.
Figure 8:
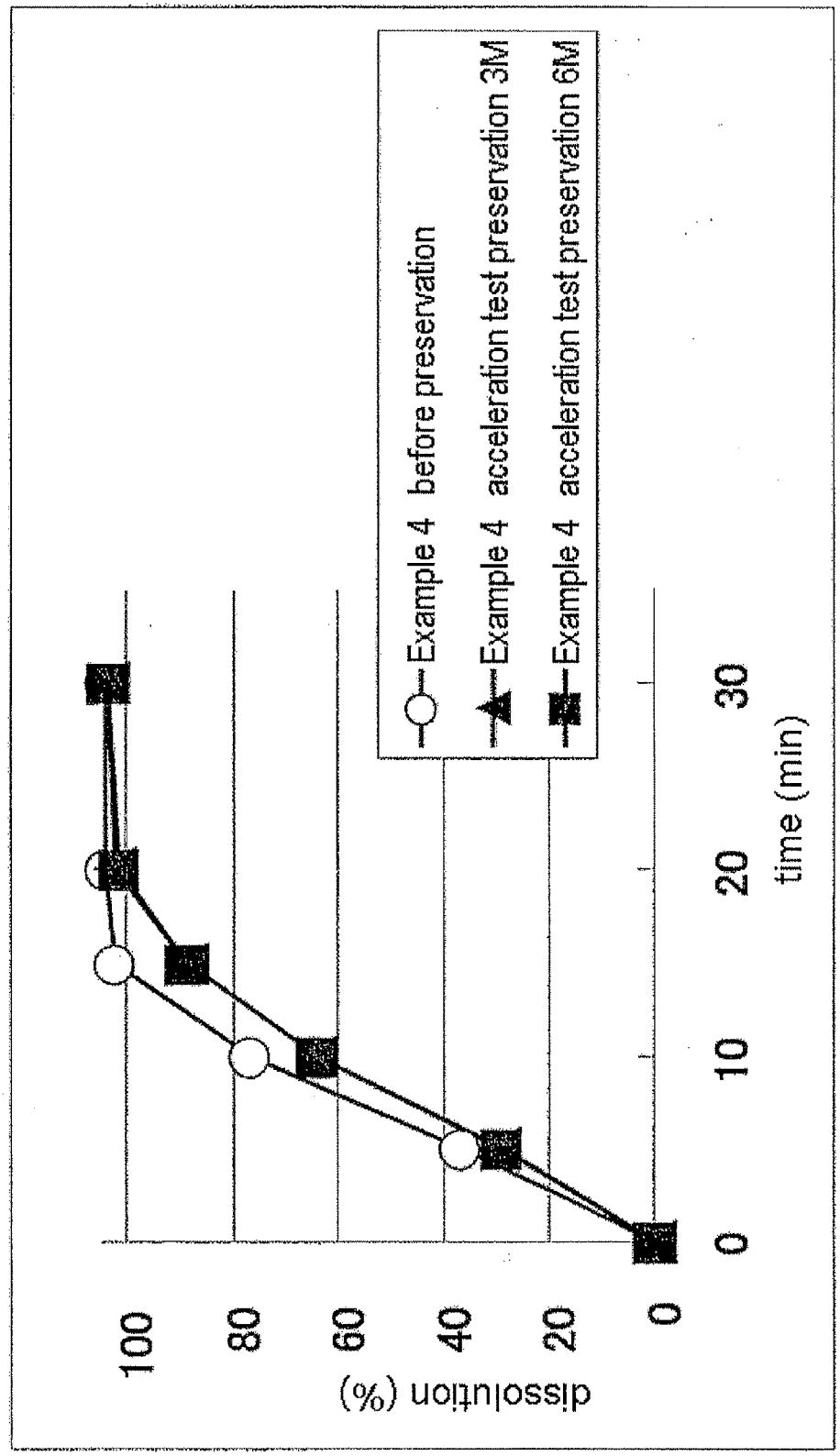
FIG. 8 shows the comparison results of the dissolution ratios of the preparation of Example 4 before and after preservation.

The results of Comparative Examples 1-3 are shown in FIGS. 3-5. The results of Examples 2-4 are shown in FIGS. 6-8. As is clear from FIGS. 1-3, the tenegliptin preparations (Comparative Examples 1-3) produced according to conventional preparation formulation showed delayed dissolution after a long-term preservation. In contrast, as is clear from FIGS. 6-8, the solid preparation of the present invention did not show delayed dissolution even after a long-term preservation.

Experimental Example 2

Comparative Test of Dissolution Ratio Before and After Preservation of Preparation Using Different Excipient The preparations obtained in Examples 5 and 6 were blister packaged and subjected to an acceleration test. The dissolution ratio of the main drug was compared between before preservation and after preservation (40° C., 75% RH, 3 months or 6 months). The dissolution ratio was calculated by adding the preparations before and after preservation to the Japanese Pharmacopoeia Second Solution (900 mL) heated to 37° C., stirring the mixture at paddle rotation 50 rpm and measuring the concentration of the main drug over time.

Figure 9:
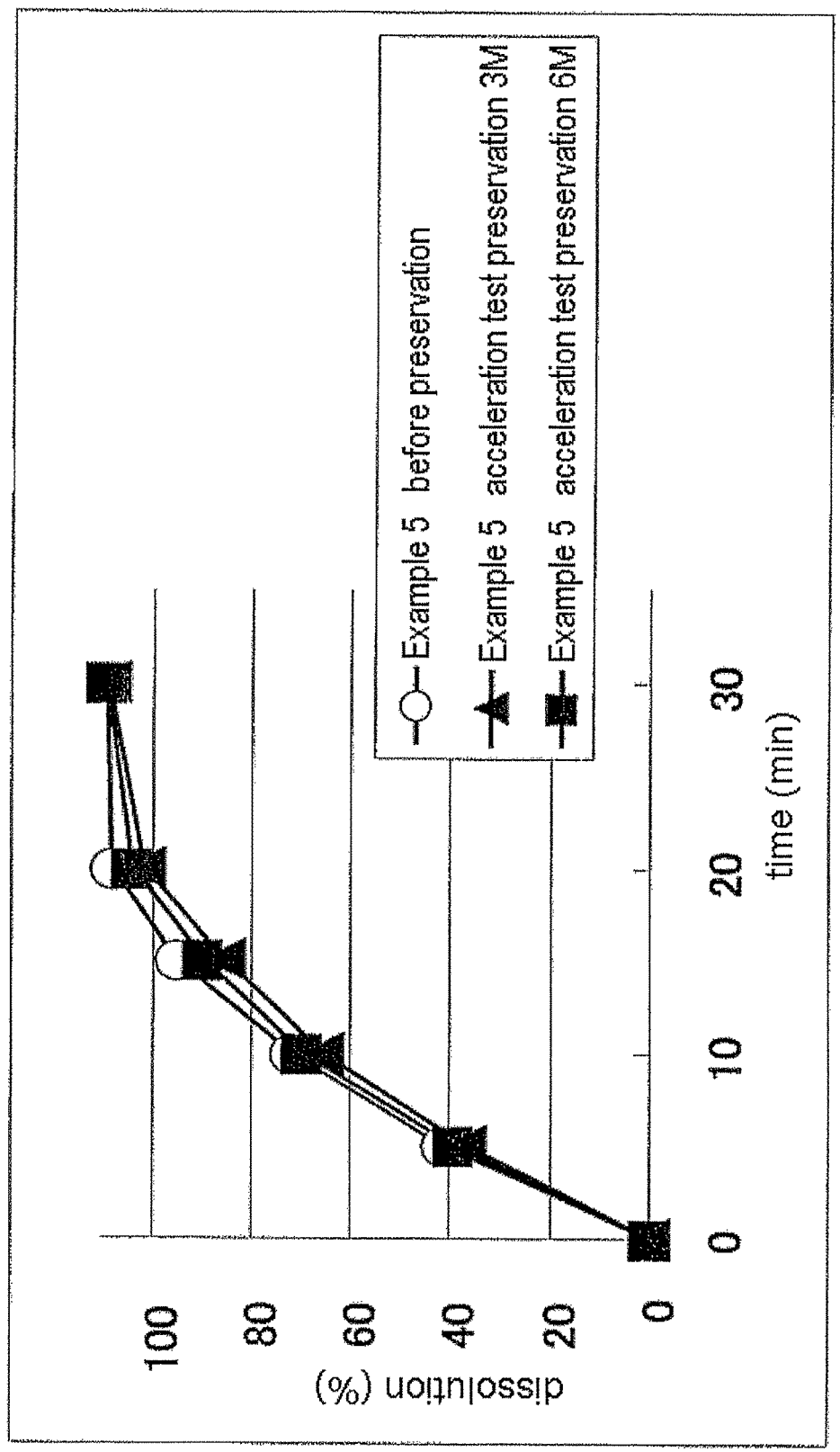
FIG. 9 shows the comparison results of the dissolution ratios of the preparation of Example 5 before and after preservation.
Figure 10:
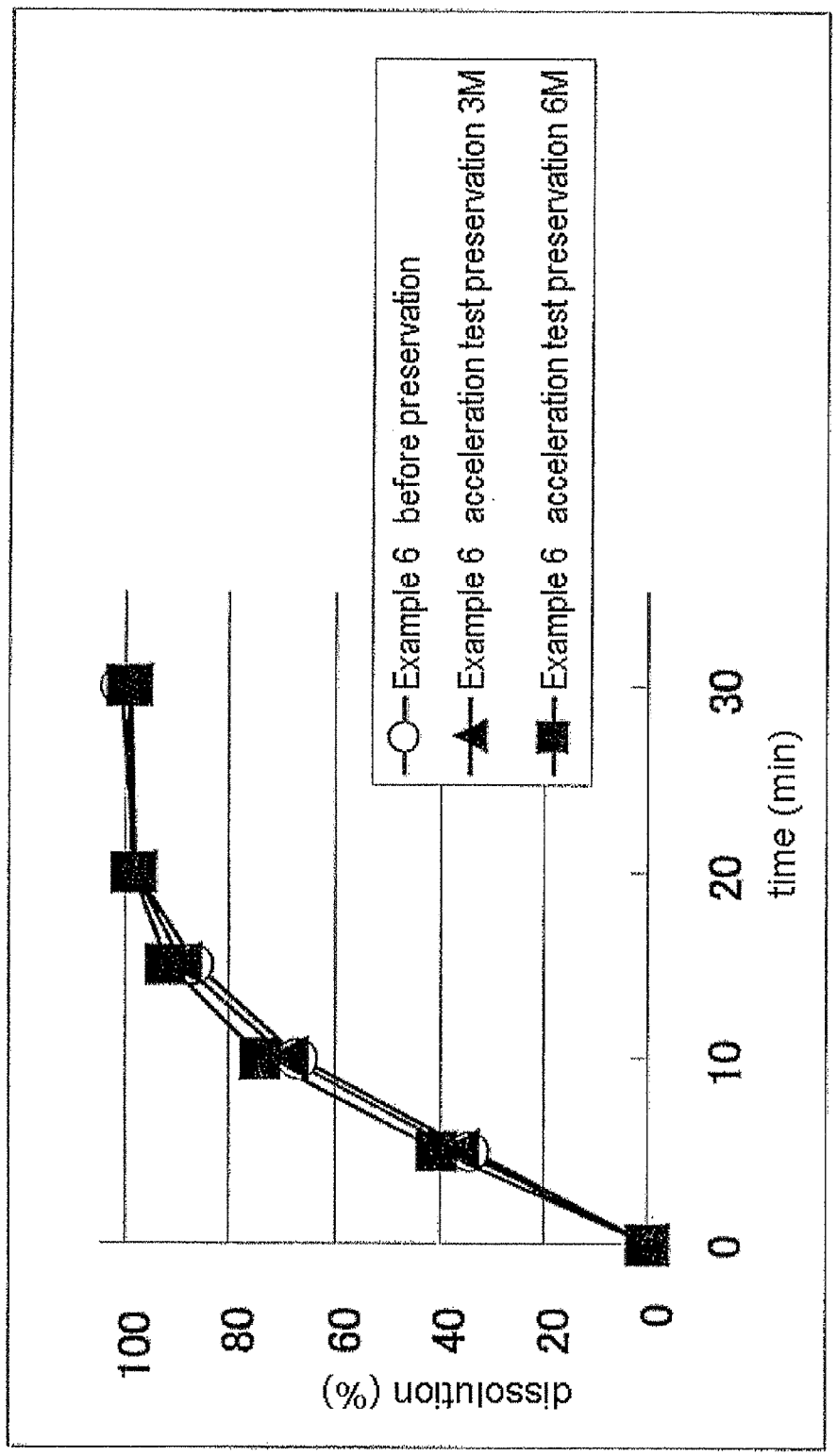
FIG. 10 shows the comparison results of the dissolution ratios of the preparation of Example 6 before and after preservation.

The results are shown in FIGS. 9 and 10. As is clear from FIGS. 9 and 10, the solid preparation of the present invention did not show delayed dissolution even after a long-term preservation.

Experimental Example 3

Comparative Test of Dissolution Ratio Before and After Preservation of Preparation Using Excipient having Different Particle Diameter The preparations obtained in Examples 7 and 8 were blister packaged and subjected to an acceleration test. The dissolution ratio of the main drug was compared between before preservation and after preservation (40° C., 75% RH, 3 months or 6 months). The dissolution ratio was calculated by adding the preparations before and after preservation to the Japanese Pharmacopoeia Second Solution (900 mL) heated to 37° C., stirring the mixture at paddle rotation 50 rpm and measuring the concentration of the main drug over time.

Figure 11:
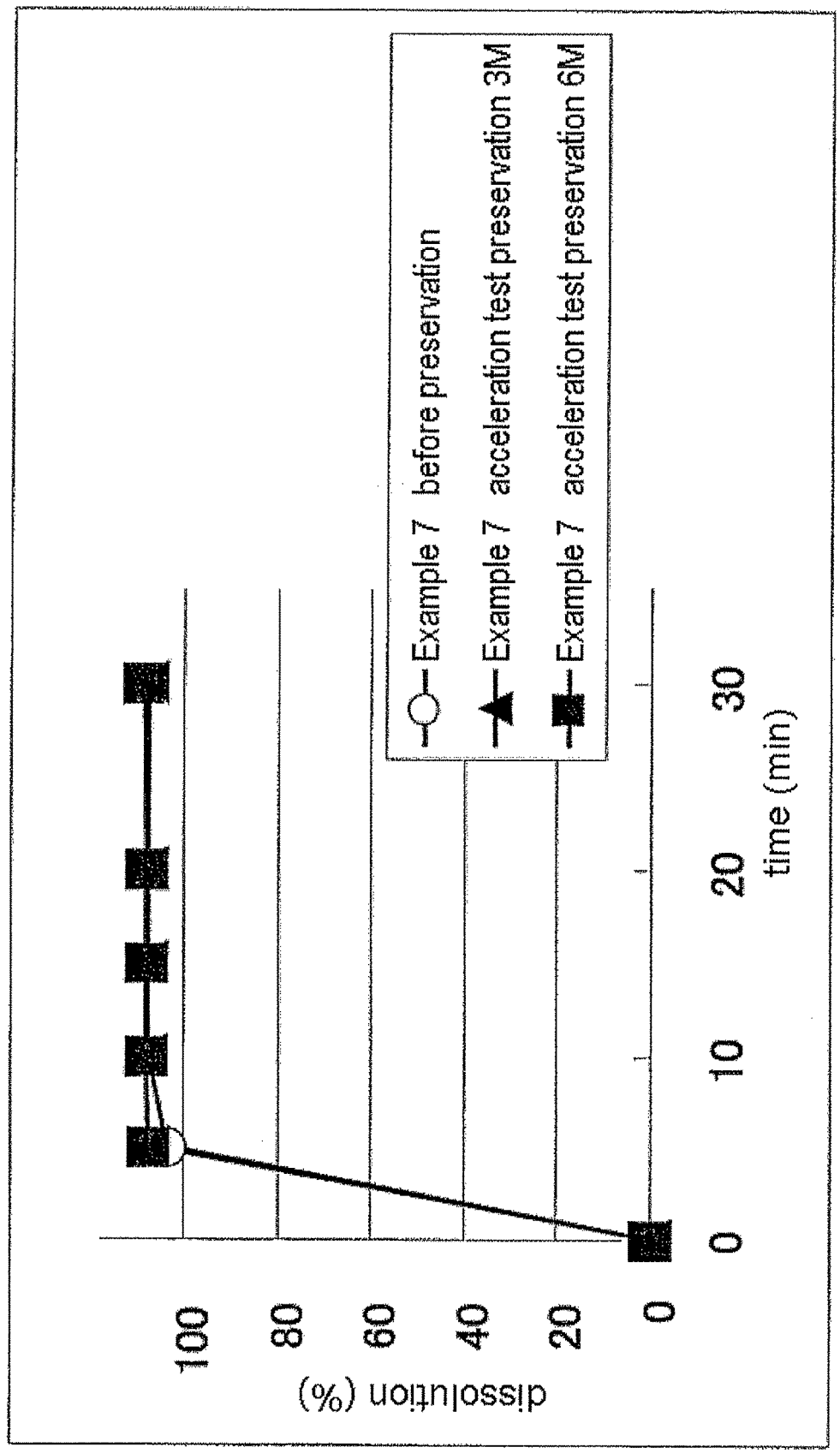
FIG. 11 shows the comparison results of the dissolution ratios of the preparation of Example 7 before and after preservation.
Figure 12:
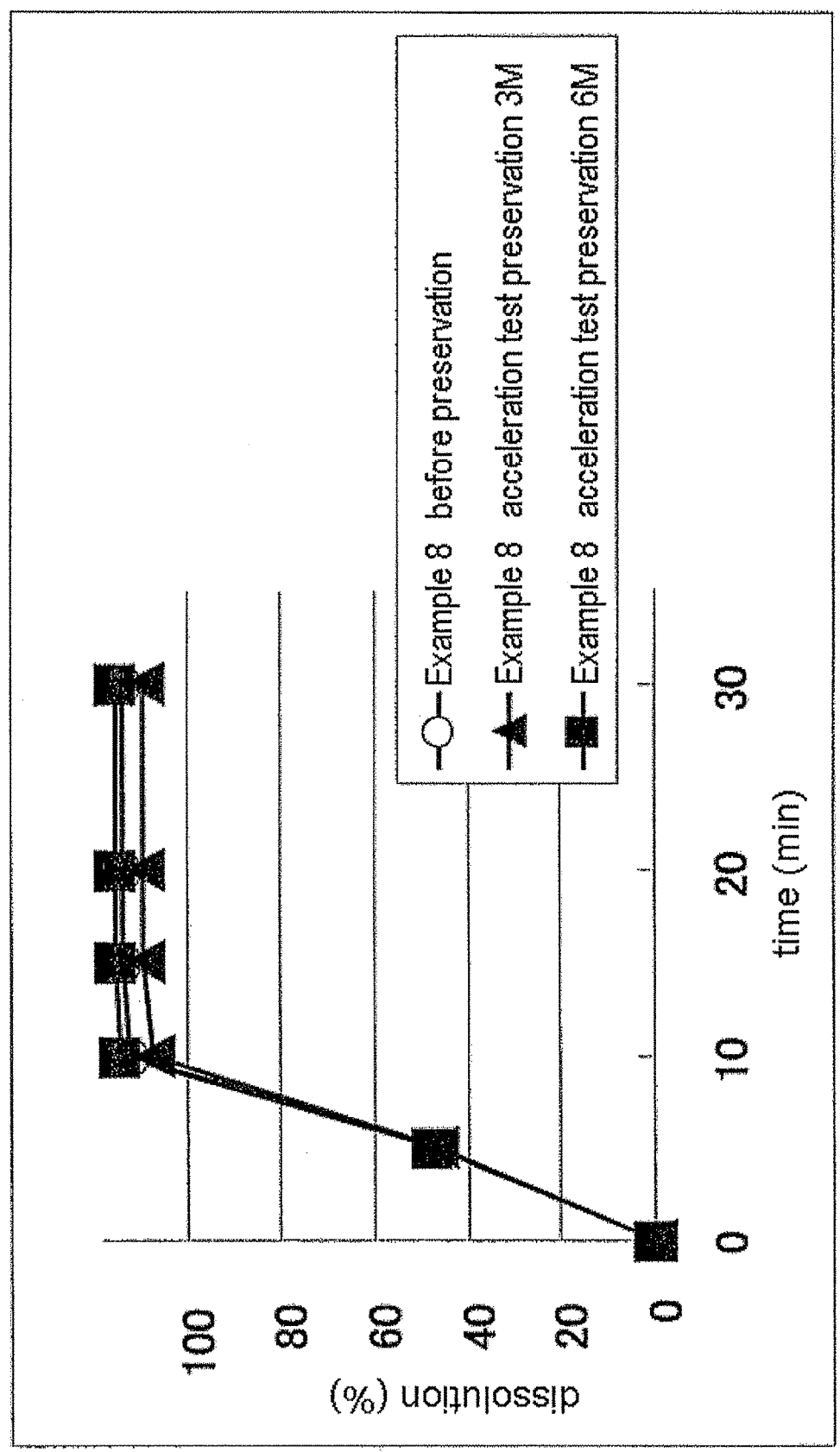
FIG. 12 shows the comparison results of the dissolution ratios of the preparation of Example 8 before and after preservation.

The results are shown in FIGS. 11 and 12. As is clear from FIGS. 11 and 12, the solid preparation of the present invention did not show delayed dissolution even after a long-term preservation.

INDUSTRIAL APPLICABILITY

According to the present invention, delayed dissolution of the active ingredient after a long-term preservation, which is seen in conventional tenegliptin-containing solid preparations, can be improved, and the content of the main drug can be easily adjusted. Therefore, the present invention is useful for the production of a therapeutic drug for type 2 diabetes, which contains tenegliptin, and the like.

This application is based on a patent application No. 2009-287809 filed in Japan, the contents of which are incorporated in full herein.

The invention claimed is:

1. A tenegliptin-containing solid preparation comprising (i) a tenegliptin-containing part containing tenegliptin hydrobromide hydrate, and (ii) a part other than the tenegliptin-containing part that does not comprise tenegliptin hydrobromide hydrate,
  wherein
    the content of tenegliptin hydrobromide hydrate in the tenegliptin-containing part is 30 to 80 wt %, the part other than the teneligliptin-containing part comprises an excipient with a volume average particle diameter of 50 μm to 500 μm, and the teneligliptin-containing part is particulate or granular and discrete particles or granules of the teneligliptin-containing part are dispersed throughout the part other than the teneligliptin-containing part.

2. The solid preparation according to claim 1, wherein the excipient contained in a part other than the teneligliptin-containing part is one or more selected from D-mannitol, sorbitol and xylitol.

3. The solid preparation according to claim 1, wherein the excipient contained in the part other than the teneligliptin-containing part has an average particle diameter of 100 μmm to 300 μmm.

4. The solid preparation according to claim 1, wherein the teneligliptin-containing part contains D-mannitol or xylitol.

5. The solid preparation according to claim 4, wherein the part other than the teneligliptin-containing part contains one or more excipients selected from D-mannitol, sorbitol and xylitol.

6. The solid preparation according to claim 5, wherein the content percentage of teneligliptin hydrobromide hydrate in the teneligliptin-containing part is 45 to 55 wt %.

7. The solid preparation according to claim 1, wherein the content percentage of the teneligliptin hydrobromide hydrate in the teneligliptin-containing part is 45 to 55 wt %.

* * * * *